United States Patent [19]

Hamilton et al.

[11] Patent Number: 4,937,270
[45] Date of Patent: Jun. 26, 1990

[54] WATER INSOLUBLE DERIVATIVES OF HYALURONIC ACID

[75] Inventors: Raymond Hamilton, Somerville, Mass.; Ellen M. Fox, Cranston, R.I.; Raksha A. Acharya, Northboro; Alan E. Walts, Brookline, both of Mass.

[73] Assignee: Genzyme Corporation, Boston, Mass.

[21] Appl. No.: 100,104

[22] Filed: Sep. 18, 1987

[51] Int. Cl.$^5$ ............................................. A61K 47/26
[52] U.S. Cl. ...................................... 514/777; 424/7.1; 424/488; 536/4.1; 252/315.3
[58] Field of Search ...................... 252/315.3; 514/777; 424/7.1, 488; 536/4.1

[56] References Cited

U.S. PATENT DOCUMENTS 4,582,865 4/1986 Balazs et al. ........................... 524/29
4,774,093 9/1988 Provonchee et al. ................. 536/4.1

FOREIGN PATENT DOCUMENTS 0193510 2/1986 European Pat. Off.
86/00079 6/1985 PCT Int'l Appl.
86/00912 7/1985 PCT Int'l Appl.
8420560 8/1984 United Kingdom.

OTHER PUBLICATIONS

Sparer et al., "Controlled Release from Glycosaminoglycan Drug Complexes", Chapter 6, *Controlled Release Delivery Systems*.

I. Danishefsky et al., "Conversion of Carboxyl Groups of Mucopolysaccharides into Amides of Amino Acid Esters", *Carbohydrate Research*—An Internation Journal.

T. C. Laurent et al., "Cross-Linked Gels of Hyaluronic Acid", *Acta Chemica Scandinavica*, vol. 18, 1984, No. 1, (1-282).

*Primary Examiner*—Mark L. Bell
*Assistant Examiner*—David M. Brunsman
*Attorney, Agent, or Firm*—Fish & Richardson

[57] ABSTRACT

A method for making a water insouble bicompatible gel includes activating HA with an activating agent to form activated HA, and reacting the activated HA with a nucleophile, under conditions producing the water insoluble bicompatible gel. Also, a method for making a water insoluble biocompatible film includes providing a biocompatible gel made according to the above method, and drying the gel or compressing the gel under conditions permitting escape of water from the gel. Also, a water insoluble composition including HA is prepared without the use of any bifunctional or polyfunctional nucleophile.

42 Claims, No Drawings

WATER INSOLUBLE DERIVATIVES OF HYALURONIC ACID

BACKGROUND OF THE INVENTION

The present invention relates to biocompatible films and gels formed from chemically modified hyaluronic acid.

Hyaluronic acid ("HA") is a naturally occuring mucopolysaccharide found, for example, in synovial fluid, in vitreous humor, in blood vessel walls and umbilical cord, and in other connective tissues. The polysaccharide consists of alternating N-acetyl-D-glucosamine and D-glucuronic acid residues joined by alternating $\beta$ 1-3 glucuronidic and $\beta$ 1-4glucosaminidic bonds, so that the repeating unit is -(1→4)-$\beta$-D-GlcA-(1→3)-$\beta$-D-GlcNAc-. In water, hyaluronic acid dissolves to form a highly viscous fluid. The molecular weight of hyaluronic acid isolated from natural sources generally falls within the range of $5 \times 10^4$ up to $1 \times 10^7$ daltons.

As used herein the term "HA" means hyaluronic acid and any of its hyaluronate salts, including, for example, sodium hyaluronate (the sodium salt), potassium hyaluronate, magnesium hyaluronate, and calcium hyaluronate.

HA, in chemically modified ("derivatized") form, is useful as a surgical aid, to prevent adhesions or accretions of body tissues during the post-operation period. The derivatized HA gel or film is injected or inserted into the locus between the tissues that are to be kept separate to inhibit their mutual adhesion. To be effective the gel must remain in place and prevent tissue contact for a long enough time so that when the gel finally disperses and the tissues do come into contact, they will no longer have a tendency to adhere.

Chemically modified HA can also be useful for controlled release drug delivery. Balazs et al., 1986, U.S. Pat. No. 4,582,865, states that "cross-linked gels of HA can slow down the release of a low molecular weight substance dispersed therein but not covalently attached to the gel macromolecular matrix." R. V. Sparer et al., 1983, Chapter 6, pages 107-119, in T. J. Roseman et al., *Controlled Release Delivery Systems*, Marcel Dekker, Inc., New York, describes sustained release of chloramphenicol covalently attached to hyaluronic acid via ester linkage, either directly or in an ester complex including an alanine bridge as an intermediate linking group.

I. Danishefsky et al., 1971, Carbohydrate Res., Vol. 16, pages 199-205, describes modifying a mucopolysaccharide by converting the carboxyl groups of the mucopolysaccharide into substituted amides by reacting the mucopolysaccharide with an amino acid ester in the presence of 1-ethyl-3-(3-dimethylaminopropyl) carbodiimide hydrochloride ("EDC") in aqueous solution. They reacted glycine methyl ester with a variety of polysaccharides, including HA. The resulting products are water soluble; that is, they rapidly disperse in water or in an aqueous environment such as is encountered between body tissues.

Proposals for rendering HA compositions less water soluble include cross-linking the HA. R. V. Sparer et al., 1983, Chapter 6, pages 107-119, in T. J. Roseman et al., *Controlled Release Delivery Systems*, Marcel Dekker, Inc., New York, describe modifying HA by attaching cysteine residues to the HA via amide bonds and then cross-linking the cysteine-modified HA by forming disulfide bonds between the attached cysteine residues. The cysteine-modified HA was itself water soluble and became water insoluble only upon cross-linking by oxidation to the disulfide form.

De Belder et al., PCT Publication No. WO 86/00912, describe a slowly-degradable gel, for preventing tissue adhesions following surgery, prepared by cross-linking a carboxyl-containing polysaccharide with a bi- or polyfunctional epoxide. Other reactive bi- or polyfunctional reagents that have been proposed for preparing cross-linked gels of HA having reduced water solubility include: 1,2,3,4-diepoxybutane in alkaline medium at 50° C. (T. C. Laurent et al., 1964, Acta Chem. Scand., Vol. 18, page 274); divinyl sulfone in alkaline medium (E. A. Balasz et al., U.S. Pat. No. 4,582,865, (1986); and a variety of other reagents including formaldehyde, dimethylolurea, dimethylolethylene urea, ethylene oxide, a polyaziridine, and a polyisocyanate (E. A. Balasz et al., U. K. Patent Appl. No. 84 20 560 (1984). T. Malson et al., 1986, PCT Publication No. WO 86/00079, describe preparing cross-linked gels of HA for use as a vitreous humor substitute by reacting HA with a bi- or polyfunctional cross-linking reagent such as a di- or polyfunctional epoxide. T. Malson et al., 1986, EPO 0 193 510, describe preparing a shaped article by vacuum-drying or compressing a cross-linked HA gel.

SUMMARY OF THE INVENTION

In general, the invention features, in one aspect, a method for making a water insoluble biocompatible gel, the method including activating HA with an activating agent to form activated HA, and reacting the activated HA with a nucleophile, under conditions producing the water insoluble biocompatible gel.

In preferred embodiments, the activation and the reaction occur concurrently; the activation includes providing an aqueous mixture including the HA, lowering the pH of the aqueous mixture to between 4.0 and 0.5 by addition of an acid, and then contacting the aqueous mixture with the activating agent; the aqueous mixture includes a concentration of the HA in the range between 0.4% and 2.6% w/w; the acid includes hydrochloric acid; the HA and the activating agent are present during the activation at a molar ratio of at least 0.2 molar equivalent of activating agent to 1 molar equivalent of glucuronic acid residues of the HA; the activated HA and the nucleophile are present in the reacting step at a molar ratio of at least 0.2 molar equivalent of the nucleophile to 1 molar equivalent of glucuronic acid residues of the activated HA; the activating agent includes a carbodiimide (preferably 1-ethyl-3-(3-dimethylaminopropyl) carbodiimide or 1-ethyl-3-(3-dimethylaminopropyl) carbodiimide methiodide); and the nucleophile includes an amino acid amide (preferably leucinamide hydrochloride), a monofunctional amine (preferably aniline), an amino acid, a salt of an amino acid, or an ester (preferably a methyl ester or a butyl ester, including a t-butyl ester) of an amino acid selected from the group comprising leucine, valine, isoleucine, arginine, proline, histidine, or phenylalanine (preferably L-leucine methyl ester hydrochloride, L-valine methyl ester hydrochloride, L-isoleucine methyl ester hydrochloride, L-arginine methyl ester hydrochloride, L-proline methyl ester hydrochloride, L-histidine methyl ester hydrochloride, L-phenylalanine hydrochloride, or L-leucine t-butyl ester hydrochloride; the method further includes admixing a detectable marker (preferably a dye that stains amino acids, including "Brilliant Blue R").

In another aspect, the invention features a gel made according to the above method.

In another aspect the invention features a method for making a water insoluble biocompatible film, the method including providing the biocompatible gel and drying the gel or compressing the gel under conditions permitting escape of water from the gel.

In another aspect the invention features a film made according to the above method.

In another aspect the invention features a water insoluble composition including HA, the composition being substantially free of crosslinking, substantially free of any bifunctional or polyfunctional nucleophile, and substantially free of any bifunctional or polyfunctional electrophile.

In preferred embodiments the composition further includes a monofunctional nucleophile including a monofunctional amine; a detectable marker; a pharmaceutically active substance (preferably either covalently bonded to the HA or dispersed within the composition and not covalently bonded to the composition).

In another aspect the invention features a water insoluble composition including the reaction product of HA, an activating agent, and a nucleophile.

The term "film", as used herein, means a substance formed by compressing a gel or by allowing or causing a gel to dehydrate, and any gel of the invention may be formed into such a film.

A "biocompatible" substance, as that term is used herein, is one that has no medically unacceptable toxic or injurious effects on biological function.

We have discovered that by treating HA with a suitable activating agent and a nucleophile, a gel or film may be made having decreased water solubility and in which the HA is covalently modified at the carboxyl groups, without the use of any bi- or polyfunctional cross-linking reagent. A "water soluble" gel or film, as that term is used herein, is one which, formed by drying an aqueous solution of 1% weight/weight ("w/w") sodium hyaluronate in water, having dimensions 3 cm × 3 cm × 0.3 mm, when placed in a beaker of 50 ml of distilled water at 20° C. and allowed to stand without stirring, loses its structural integrity as a film after 3 minutes, and becomes totally dispersed within 20 minutes. A "water insoluble" film of the invention, as that phrase and like terms are used herein, formed using a 1% aqueous solution of HA, modified according to the invention, having the same dimensions and similarly allowed to stand without stirring in a beaker of 50 ml of distilled water at 20° C., is structurally intact after 20 minutes; the film boundaries and edges are still present after 24 hours, although the film is swollen.

HA is said to be "activated", as that term is used herein, when it is treated in an aqueous mixture in a manner that renders the carboxyl groups on the HA vulnerable to nucleophilic attack; and an "activating agent" is a substance that, in an aqueous mixture including HA, causes the HA to become so activated.

Under various reaction conditions various nucleophiles can be used to modify the activated HA. A "nucleophile", as used herein, is any molecule possessing an electron rich functional group (preferably a primary amine) capable of reacting with activated HA.

No cross-linking agents are employed in the manufacture or use of the gels or films of the invention. A "cross-linking agent", as used herein, is a molecule containing two or more nucleophilic moieties (such as, e.g., amino groups) capable of reacting with activated HA, or is a molecule containing two or more electrophilic moieties capable of reacting with the hydroxyl groups of HA. Preferred nucleophiles are those which are biocompatible, although any nucleophile capable of reacting with activated HA so as to give a biocompatible product may be used. Moreover, because the gels and films are water insoluble, they can be thoroughly washed with water before use to remove unreacted substances.

Films and gels of the invention can also be prepared in colored form, by including a dye or stain in the reaction mixture. Such colored films and gels can be more easily seen when in place or during placement, making them easier to handle during surgical procedures than colorless ones.

Because they are biocompatible and water insoluble, the gels and films of the invention can be particularly useful as surgical aids where tissues are to be displaced or separated for an extended period of time, such as, for example, a period of time sufficient to permit healing of a wound.

DESCRIPTION OF THE PREFERRED EMBODIMENT

The gels and films of the invention are made generally as follows. HA is dissolved in water and the pH of the resulting aqueous mixture is adjusted downward; then the dissolved HA is activated by admixing a suitable activating agent, and a suitable nucleophile is admixed with the activated HA and allowed to stand until the desired gel has formed. The activating agent and the nucleophile can be admixed in any sequence.

The preferred method of making the gels and films of the invention will now be described in more detail. As one skilled in the art will appreciate, gels and films of the invention can be made using protocols that are within the method of the invention yet are different in particulars from those described here.

A sample of hyaluronic acid or a salt of hyaluronic acid, such as sodium hyaluronate, is dissolved in water to make an aqueous mixture. HA from any of a variety of sources can be used. As is well-known, HA can be extracted from animal tissues or harvested as a product of bacterial fermentation. Hyaluronic acid can be produced in commercial quantities by bioprocess technology, as described for example in PCT Publication No. WO 86/04355. Preferably the concentration of HA in this first aqueous mixture is in the range between 0.4% and 2.6% weight/weight ("w/w"). Subsequent reactions are slower and less effective at significantly lower concentrations, while significantly higher concentrations are difficult to handle owing to their high viscosity.

The aqueous HA mixture should be acidic, preferably having a pH between pH 4.0 and pH 5.0, more preferably between pH 4.75 and pH 5.0, and most preferably pH 4.75. At lower pH values the preferred activating agent, EDC, is unstable, and at higher values the reaction rate is diminished. Preferably hydrochloric acid is added to adjust the pH, although other known acids can be used.

Once the pH of the aqueous mixture has been adjusted, an activating agent is admixed. Preferred activating agents include carbodiimides, most preferably EDC (in some references this substance is termed 1-(3-dimethylaminopropyl)-3-ethyl-carbodiimide or "DEC") or ETC (1-(3-dimethylaminopropyl)-3-ethyl-carbodiimide methiodide).

Then a nucleophile is admixed to the aqueous HA-activating agent mixture. Preferred nucleophiles include certain amino acid esters, more preferably the methyl esters of leucine, isoleucine, valine, phenylalanine, histidine, or proline, and most preferably L-leucine methyl ester hydrochloride. Other substituted esters of amino acids can be used including, e.g., ethyl and t-butyl esters, and other monofunctional amines can be used such as, e.g., aniline.

The nucleophile and the activating agent may be admixed to the pH adjusted HA mixture in any sequence, either all at once or gradually.

If a colored product is desired, a solution of a dye or stain such as the blue dye "Brilliant Blue R", also known as "Coomassie ® Brilliant Blue R-250", distributed as "Serva Blue" by Serva, can be admixed to the reaction mixture at this point. The resulting product has a blue color that can provide a good contrast to the color of body tissues, making the film or gel easy to see while it is handled during surgery and once it is in place.

Once the reagents (and the stain or dye, if any) have been admixed, the reaction mixture can be simply allowed to stand for a time, or it can be continually or occasionally stirred or agitated.

Upon admixing of the reagents the pH rises, and can be maintained at pH 4.75 by addition of acid as the reaction proceeds. We have found, however, that films and gels with various desired physical properties can be obtained by simply allowing the pH to rise as the reaction proceeds. The mode of addition of the reagents, particularly the EDC and the nucleophile, is not critical, but the ratios of these reagents to the HA is important. We have found that a ratio of one molar equivalent of glucuronic acid residues to 1.6 molar equivalents of EDC results in strong gels while a ratio of 1:0.2 results in weak gels which collapse to fluid solutions over a period of several days. Thus, although the ratios of EDC and nucleophile to HA can vary over a wide range, ratios of EDC to HA or of nucleophile to HA of greater than 0.2:1 are preferred. The more preferred ratio depends on the particular nucleophile being used and the desired physical properties of the final product. Lower values typically result in weaker, less insoluble products, while higher values typically result in stronger, more insoluble products.

HA modified according to the above descriptions can be cast as films in a straightforward manner. Typically the reaction mixture is poured into a vessel having the desired size and shape and allowed to air dry. In general films formed by drying mixtures poured thickly, so that they have a lower surface area/volume, possess greater strength than films formed by drying thinner, higher surface area/volume mixtures.

Alternatively a film can be formed by compressing a gel under conditions that permit escape of water, as, for example, by compressing the gel between two surfaces, at least one of which is porous, as described, for example, in EPO 0 193 510.

If desired, a gel or film can be washed prior to use by, for example, perfusion with water or 1M aqueous sodium chloride. Alternatively the reaction mixture can be dialyzed to remove residual reagents prior to casting as a film. Washing to remove residual reagents or reagent-derived material such as substituted ureas is desirable if the film or gel is to be used for therapeutic applications. Gels or films colored blue with Brilliant Blue R as described above do not lose their coloration during such washing. The removal of reagents or reaction products can be monitored by high pressure liquid chromatography.

DETAILED DESCRIPTION OF THE INVENTION

The invention is described in more detail in the following examples. These examples are given by way of illustration and are not intended to limit the invention except as set forth in the claims.

EXAMPLE 1

In this example hydrogels were prepared using EDC as an activating agent and leucine methyl ester hydrochloride as a nucleophile.

Sodium hyaluronate (400 mg; 1.0 mmol of carboxyl groups) having a molecular weight between $1 \times 10^6$ and $2 \times 10^6$ was dissolved in 10 ml of distilled water. The pH of the aqueous solution was adjusted to pH 4.75 by addition of 0.1N HCl. Then 314 mg of EDC (1.64 mmol) was added all at once followed by 190 mg (1.05 mmol) of L-leucine methyl ester hydrochloride. The pH of the reaction mixture then rose to 6.2 over two hours. The reaction mixture was kept at room temperature for five hours, after which time it had formed a thick insoluble hydrogel. This hydrogel could be washed with a 1M NaCl solution to remove residual reagents without loss of its physical properties.

EXAMPLE 2

In this example various EDC/leucine:HA ratios were used for comparison of gel formation and properties.

The procedure was as in Example 1, using sodium hyaluronate (400 mg; 1.0 mmol of carboxyl groups) in 15 ml of water. In separate experiments the following quantities of EDC and leucine methyl ester hydrochloride were then added: 153 mg EDC (0.8 mmol)/182 mg leucine methyl ester hydrochloride (1.0 mmol); 76 mg EDC (0.4 mmol)/90 mg leucine methyl ester hydrochloride (0.5 mmol); and 38 mg EDC (0.2 mmol)/45 mg leucine methyl ester hydrochloride (0.25 mmol). Strong hydrogels were obtained as in example 1 for the highest ratio of EDC and leucine methyl ester hydrochloride. At the lowest ratio of reactants (0.2 mmol/0.25 mmol to 1.0 mmol HA carboxyl groups) a weak gel was obtained, which collapsed to a fluid after two weeks.

EXAMPLE 3

In this example the HA concentration was reduced by one-half for comparison of resulting gel properties.

The procedure was as in example 1 except the HA (400 mg; 1.0 mmol of carboxyl groups) was dissolved in 30 ml of water rather than 15 ml (1⅓% w/w HA). A hydrogel was formed, although it was weaker than that obtained in Example 1.

EXAMPLE 4

In this example films were prepared using EDC as an activating agent and leucine methyl ester hydrochloride as a nucleophile.

Sodium hyaluronate (400 mg; 1.0 mmol of carboxyl groups) was dissolved in 40 ml of distilled water. The pH of the solution was adjusted to pH 4.75 by addition of 0.1N HCl. Then EDC (314 mg; 1.64 mmol) was added in a single portion, followed by 190 mg (1.05 mmol) of L-leucine methyl ester hydrochloride. The pH of the reaction mixture rose to 6.2 during two hours, after which time the solution was poured into a petri dish of area 6360 mm², and allowed to dry to a film over a two day period. Films produced in this manner were strong and insoluble in water and 1M aqueous NaCl. The films could be washed with water or aqueous NaCl as in Example 1 to remove residual reagents without loss of their physical properties. Infrared spectroscopic analysis of such films showed no carbodiimide absorption at about 2130 $cm^{-1}$ and displayed absorptions at about 1740 $cm^{-1}$, 1700 $cm^{-1}$, 1650 $cm^{-1}$, and 1550 $cm^{-1}$.

EXAMPLE 5

In this example various HA concentrations were used in making films for comparison of resulting film properties.

The procedure described in example 4 was repeated, using three different initial HA concentrations made by dissolving the HA (400 mg; 1.0 mmol of carboxyl groups) in 30 ml, 40 ml, or 100 ml of distilled water. Films produced using each of these initial concentrations of HA were strong and insoluble in water and 1M aqueous NaCl, showing that a range of concentrations of HA can be used. Each of these films could be washed with water or aqueous NaCl without loss of its physical properties.

EXAMPLE 6

This example illustrates the effect of dialyzing the reaction mixture prior to casting to form a film, as compared with washing the film after forming it.

Sodium hyaluronate (400 mg in 40 ml of water), EDC (314 mg; 1.64 mmol) and L-leucine methyl ester hydrochloride (190 mg; 1.05 mmol) were allowed to react as in Example 4. Upon completion of reaction (2 hours) the reaction mixture was dialyzed against water, through 12,000 NMW cutoff dialysis tubing in order to remove residual reagents. The dialyzed mixture was then cast as a film as in Example 4. The film so obtained was strong and insoluble in water or 1M aqueous NaCl.

EXAMPLE 7

In this example films were formed by drying more thickly poured reaction mixtures, to compare the properties of films produced from drying mixtures at differing surface area/volume.

A reaction mixture obtained as in Example 4 (40 ml reaction volume) was cast into a small petri dish (area 3330 mm²). The film so obtained was insoluble in 1M aqueous NaCl and in water (100° C.; 1 hour).

EXAMPLE 8

In this example films were prepared using other amino acid esters and HA activated with EDC.

A solution of HA (400 mg in 40 ml of H₂O) was brought to pH 4.7 using 0.1N HCl. Then EDC (314 mg; 1.6 mmol) was added all at once followed by 1 mmol of the amino acid derivative. The reaction mixture was poured into a petri dish and allowed to dry. Insoluble films were obtained from L-valine methyl ester hydrochloride, L-isoleucine methyl ester hydrochloride, L-proline methyl ester hydrochloride, and L-phenylalanine methyl ester hydrochloride.

EXAMPLE 9

In this example films were prepared using a simple primary amine (aniline) as a nucleophile.

A solution of HA (400 mg in 40 ml of H₂O) was brought to pH 4.7 using 0.1N HCl. Then EDC (314 mg; 1.6 mmol) was added all at once followed by 1 mmol of aniline. The reaction mixture was poured into a petri dish and allowed to dry, and insoluble films were obtained.

EXAMPLE 10

In this example films were prepared using other esters of leucine.

A solution of HA (400 mg in 40 ml of H₂O) was brought to pH 4.7 using 0.1N HCl. Then EDC (314 mg; 1.6 mmol) was added all at once followed by 1 mmol of the leucine ester. The reaction mixture was poured into a petri dish and allowed to dry. Insoluble films were obtained from both L-leucine ethyl ester hydrochloride and L-leucine t-butyl ester hydrochloride.

EXAMPLE 11

In this example gels were prepared using other amino acid methyl esters.

A solution of HA (400 mg in 15 ml of H₂O) was brought to pH 4.7 and EDC (314 mg; 1.6 mmol) was added, followed by the amino acid derivative (1 mmol). The reaction mixture formed a thick gel within from 5 to 24 hours. Water insoluble gels were obtained using L-valine methyl ester hydrochloride, L-isoleucine methyl ester hydrochloride, L-arginine methyl ester hydrochloride, L-proline methyl ester hydrochloride, and L-histidine methyl ester hydrochloride.

EXAMPLE 12

In this example films were prepared using an amino acid amide (leucinamide) as a nucleophile.

A solution of HA (400 mg in 40 ml of H₂O) was brought to pH 4.7 using 0.1N HCl. Then EDC (314 mg; 1.6 mmol) was added all at once followed by 1 mmol of L-leucinamide hydrochloride. The reaction mixture was poured into a petri dish and allowed to dry and insoluble films were obtained.

EXAMPLE 13

In this example gels were prepared using leucine ethyl ester hydrochloride.

A solution of HA (400 mg in 15 of H₂O) was brought to pH 4.7 and EDC (314 mg; 1.6 mmol) was added, followed by leucine ethyl ester hydrochloride (1.0 mmol). The mixture formed a thick, water insoluble gel within from 5 to 24 hours.

EXAMPLE 14

In this example films and gels were prepared using ETC as the HA activating agent.

Sodium hyaluronate (400 mg, 1.0 mmol of carboxyl groups) having a molecular weight in the range between $1 \times 10^6$ and $2 \times 10^6$ daltons was dissolved in water (10 ml and 30 ml). The pH of each aqueous solution was adjusted to pH 4.75 by addition of 0.1N HCl. Then 475 mg of ETC (1.6 mmol) was added all at once, followed by 190 mg (1.05 mmol) of L-leucine methyl ester hydrochloride. The pH of this reaction mixture rose to pH 6.2 over the next 2 hours. The reaction mixture containing 10 ml of water formed an insoluble gel. The reaction mixture containing 30 ml of water gave an insoluble film after drying.

EXAMPLE 15

This example illustrates the preparation of a colored film.

A solution of HA (400 mg in 30 ml of $H_2O$) was brought to pH 4.75 as in example 13 and then ETC (475 mg; 1.6 mmol) and leucine methyl ester hydrochloride (190 mg; 1.05 mmol) were added. A dilute solution of "Serva Blue" (5 mg/ml) dye in $H_2O$ (0.5 ml) was then added to the reaction mixture. The resulting mixture was poured into a Petri dish and a water insoluble blue film was obtained after 16 hours. The blue color was retained by the film when the film was washed with 1M NaCl and then with $H_2O$.

EXAMPLE 16

This example illustrates the tissue biocompatibility of a film of chemically modified HA.

Four strips of films prepared according to the procedure described in Example 4, and two USP negative control strips were surgically implanted into the paravertebral muscle of White New Zealand rabbits (two per test). The test sites were evaluated either macroscopically after 72 hours or with complete histopathology after 7 days. In accordance with the USP XXI, p. 1237, the test material met the requirements of the USP Implantation Test for the Evaluation of Plastic Materials.

USE

Films or gels of the invention can be used as a surgical aid, to prevent adhesions or accretions of body tissues during a post-operation or healing period, following procedures known in the surgical arts, as described, for example, in DeBelder et al., PCT Publication No. WO 86/00912. During surgery one or more pieces of the gel or film, as appropriate, are inserted or injected between or among the tissues that are to be kept separate.

Films or gels of the invention can also be used for sustained release drug delivery. The drug to be delivered can be covalently bonded to the gel or film, as described, for example, in R. V. Sparer et al., 1983, Chapter 6, pages 107–119, in T. J. Roseman et al., *Controlled Release Delivery Systems*, Marcel Dekker, Inc., New York; and the gel or film can then be implanted or injected at the locus where delivery is desired.

OTHER EMBODIMENTS

Other embodiments are within the following claims.

We claim:

1. A method for making a water insoluble biocompatible gel, said method comprising
   providing an aqueous mixture comprising HA at a concentration in the range between 0.4% and 2.6% w/w,
   activating said HA with an activating agent to form activated HA, and
   reacting said activated HA with a nucleophile, under conditions producing said water insoluble biocompatible gel.

2. The method of claim 1 wherein said activating comprises
   providing an aqueous mixture comprising said HA,
   lowering the pH of said aqueous mixture to between 4.0 and 5.0 by addition of an acid, and then
   contacting said aqueous mixture with said activating agent.

3. The method of claim 2 wherein said aqueous mixture comprises a concentration of said HA in the range between 0.4% and 2.6% w/w.

4. The method of claim 2 wherein said acid comprises hydrochloric acid.

5. The method of claim 1 wherein said HA and said activating agent are present during said activation at a molar ratio of at least 0.2 molar equivalent of activating agent to 1 molar equivalent of glucuronic acid residues of said HA.

6. The method of claim 1 wherein said activated HA and said nucleophile are present in said reacting step at a molar ratio of at least 0.2 molar equivalent of said nucleophile to 1 molar equivalent of glucuronic acid residues of said activated HA.

7. The method of claim 1 wherein said activating agent comprises a carbodiimide.

8. The method of claim 7 wherein said carbodiimide comprises 1-ethyl-3-(3-dimethylaminopropyl) carbodiimide, or 1-ethyl-3-(3-dimethylaminopropyl) carbodiimide methiodide.

9. The method of claim 1 wherein said nucleophile comprises an amino acid.

10. The method of claim 1 wherein said nucleophile comprises an amino acid salt.

11. The method of claim 1 wherein said nucleophile comprises an amino acid ester.

12. The method of claim 11 wherein said amino acid ester comprises a methyl ester.

13. The method of claim 11 wherein said amino acid ester comprises a butyl ester.

14. The method of claim 13 wherein said butyl ester comprises a t-butyl ester.

15. The method of claim 1 wherein said nucleophile comprises a methyl ester of an amino acid from the group comprising leucine, valine, isoleucine, arginine, proline, histidine, or phenylalanine.

16. The method of claim 1 wherein said nucleophile comprises L-leucine methyl ester hydrochloride, L-valine methyl ester hydrochloride, L-isoleucine methyl ester hydrochloride, L-arginine methyl ester hydrochloride, L-proline methyl ester hydrochloride, L-histidine methyl ester hydrochloride, L-phenylalanine hydrochloride, or L-leucine t-butyl ester hydrochloride.

17. The method of claim 1 wherein said nucleophile comprises an amino acid amide.

18. The method of claim 17 wherein said amino acid amide comprises leucinamide hydrochloride.

19. The method of claim 1 wherein said nucleophile comprises a monofunctional amine.

20. The method of claim 19 wherein said monofunctional amine comprises aniline.

21. A water insoluble biocompatible gel made according to the method of claim 1.

22. A method for making a water insoluble biocompatible film, said method comprising
   providing the biocompatible gel of claim 21, and
   drying said gel.

23. The film made by the method of claim 22.

24. A method for making a water insoluble biocompatible film, said method comprising
   providing the biocompatible gel of claim 21, and
   compressing said gel under conditions permitting escape of water from said gel.

25. The film made by the method of claim 24.

26. The method of claim 1 wherein said activating and said reacting occur concurrently.

27. The method of claim 1, said method further comprising admixing a detectable marker.

28. The method of claim 22 wherein said detectable marker comprises a dye that stains amino acids.

29. The method of claim 27 wherein said detectable marker comprises "Brilliant Blue R".

30. A water insoluble composition comprising HA, said composition being substantially free of crosslinking.

31. The composition of claim 30, said composition being substantially free of any bifunctional or polyfunctional nucleophile and said composition being substantially free of any bifunctional or polyfunctional electrophile.

32. The composition of claim 30, further comprising a monofunctional nucleophile.

33. The composition of claim 30, further comprising a monofunctional amine.

34. The composition of claim 30, further comprising a detectable marker.

35. The composition of claim 34, wherein said detectable marker comprises "Brilliant Blue R".

36. The composition of claim 30, further comprising a pharmaceutically active substance.

37. The composition of claim 36 wherein said pharmaceutically active substance is covalently bonded to said HA.

38. The composition of claim 36 wherein said pharmaceutically active substance is dispersed within said composition and is not covalently bonded to said composition.

39. A water insoluble composition comprising the reaction product of HA, an activating agent, and a nucleophile.

40. The composition of claim 34, wherein said activating agent is a carbodiimide.

41. The composition of claim 40, wherein said carbodiimide is EDC.

42. The composition of claim 41, wherein said nucleophile is a methyl ester of an amino acid.

* * * * *

UNITED STATES PATENT AND TRADEMARK OFFICE
CERTIFICATE OF CORRECTION

PATENT NO. : 4,937,270

DATED : June 26, 1990

INVENTOR(S) : Raymond Hamilton et al.

It is certified that error appears in the above-identified patent and that said Letters Patent is hereby corrected as shown below:

On the face of the patent, under "OTHER PUBLICATIONS", "T.C. Laurent et al.,...." "1984" should be --1964--;

Col. 2, line 15, "Balasz" should be --Balazs--;

Col. 2 line 18, "Balasz" should be --Balazs--;

Col. 2, line 39, "0.5 by addition" should be --5.0 by addition--.

Signed and Sealed this

Ninth Day of July, 1991

*Attest:*

HARRY F. MANBECK, JR.

*Attesting Officer*   *Commissioner of Patents and Trademarks*